(12) United States Patent
Bhattacharya et al.

(10) Patent No.: US 9,201,042 B2
(45) Date of Patent: Dec. 1, 2015

(54) ARCHITECTURAL LAYOUT FOR DILUTION WITH REDUCED WASTAGE IN DIGITAL MICROFLUIDIC BASED LAB-ON-A-CHIP

(75) Inventors: Bhargab B. Bhattacharya, Kolkata, IN (US); Sudip Roy, Kolkata, IN (US); Krishnendu Chakrabarty, Chapel Hill, NC (US)

(73) Assignee: INDIAN STATISTICAL INSTITUTE, Kolkata (IN)

( * ) Notice: Subject to any disclaimer, the term of this patent is extended or adjusted under 35 U.S.C. 154(b) by 282 days.

(21) Appl. No.: 13/809,494

(22) PCT Filed: Nov. 12, 2010

(86) PCT No.: PCT/IB2010/002899
§ 371 (c)(1),
(2), (4) Date: Jan. 10, 2013

(87) PCT Pub. No.: WO2012/007787
PCT Pub. Date: Jan. 19, 2012

(65) Prior Publication Data
US 2013/0105319 A1    May 2, 2013

(30) Foreign Application Priority Data
Jul. 15, 2010   (IN) .............................. 770/KOL/2010

(51) Int. Cl.
*B81B 1/00*       (2006.01)
*G01N 27/447*     (2006.01)
(Continued)

(52) U.S. Cl.
CPC ...... *G01N 27/44791* (2013.01); *B01F 13/0071* (2013.01); *B01F 13/0076* (2013.01); *B01F 15/0404* (2013.01); *B01L 3/502792* (2013.01); *B81B 1/00* (2013.01); *B01F 2003/0896* (2013.01); *B01L 2300/0819* (2013.01); *B01L 2300/0867* (2013.01); *B01L 2300/161* (2013.01)

(58) Field of Classification Search
CPC ............ B01F 13/0071; B01F 13/0076; G01N 27/47914
See application file for complete search history.

(56) References Cited

U.S. PATENT DOCUMENTS 6,565,727 B1 *  5/2003  Shenderov .................... 204/600
6,911,132 B2    6/2005  Pamula et al.
(Continued)

FOREIGN PATENT DOCUMENTS

JP        2006-500596        1/2006
WO        WO 2010/077859     7/2010

OTHER PUBLICATIONS

Fair, "Digital microfluidics: is a true lab-on-a-chip possible?," Microfluidics and Nanofluidics, vol. 3, Jun. 2007, pp. 245-281.

(Continued)

*Primary Examiner* — Luan Van
*Assistant Examiner* — Steven Rosenwald
(74) *Attorney, Agent, or Firm* — Workman Nydegger

(57) ABSTRACT

Systems and methods are provided for producing fluids with desired concentration factors. According to one embodiment, an arrangement of digital microfluidic (DMF) based electrode platforms are provided. The arrangement may be configured to carry out a sequence of mix steps that may demand storage of resultant fluid mixtures produced in intermediate mix steps. Such sequences of mix steps may be desirable as a result of the decreased demand for initial fluid samples, and reduced wastage.

10 Claims, 8 Drawing Sheets

(51) Int. Cl.
  *B01F 13/00* (2006.01)
  *B01F 15/04* (2006.01)
  *B01L 3/00* (2006.01)
  *B01F 3/08* (2006.01)

(56) References Cited

U.S. PATENT DOCUMENTS

| | | |
|---|---|---|
| 7,569,129 B2 | 8/2009 | Pamula et al. |
| 2004/0031688 A1 | 2/2004 | Shenderov |
| 2004/0055891 A1 | 3/2004 | Pamula et al. |
| 2013/0105318 A1 | 5/2013 | Bhattacharya et al. |
| 2013/0115703 A1 | 5/2013 | Bhattacharya et al. |

OTHER PUBLICATIONS

Thies, "Programable Microfluidics", [retrieved on Mar. 2, 2011]. Retrieved from Internet; Inthttp://replay.waybackmachine.org/20090620134748/http://groups.csail.mit.edu/cag/bios; published on Jun. 20, 2009 as per Wayback Engine.

Thies, et al. "Abstraction layers for scalable microfluidic biocomputing," Natural Computing, vol. 7, Jun. 2008, pp. 255-275.

International Search Report and Written Opinion from International Application No. PCT/IB2010/002911 dated Mar. 9, 2011.

International Search Report and Written Opinion from International Application No. PCT/IB2010/002899 dated Feb. 22, 2011.

International Search Report and Written Opinion from International Application No. PCT/IB2010/002895 dated Apr. 5, 2011.

Zheng, et al., "A Microfluidic Approach for Screening Submicroliter Volumes against Multiple Reagents by Using Preformed Arrays of Nanoliter Plugs in a Three-Phase Liquid/Liquid/Gas Flow," Angewandte Chemie (International ed. in English), vol. 44, Apr. 2005, pp. 2520-2523.

Xu, et al, "Automated, Accurate, and Inexpensive Solution-Preparation on a Digital Microfluidic Biochip". Biomedical Circuits and Systems Conference, 2008. BioCAS 2008. pp. 301-304.

Yuh, et al, "Placement of Digital Microfluidic Biochips Using the T-tree Formulation" Design Automation Conference, 2006 43rd ACM. pp. 931-934.

Ding, Jie., et al., " Scheduling of Microfluidic Operations for Reconfigurable Two-dimensional Electrowetting Arrays," IEEE Transactions on Computer-Aided Design of Integrated Circuits and Systems, vol. 20,No. 12, pp. 1463-1468 (Dec. 2001).

Fair, R.B., et al., "Electrowetting-based On-chip Sample Processing for Integrated Microfluidics," IEEE IEDM'03 Technical Digest, pp. 32.5.1-32.5.4 (Dec. 2003).

Fair, R.B., et al., "Integrated Chemical/Biochemical Sample Collection, Pre-Concentration, and Analysis on a Digital Microfluidic," in Proceedings of the SPIE Conference on Lab-on-a-Chip: Platforms, Devices, and Applications, vol. 5591, pp. 113-124 (2004).

Fouillet, Y., et al ., "Digital microfluidic design and optimization of classic and new fluidic functions for lab on a chip systems," Microfluidics and Nanofluidics, vol. 4, No. 3, pp. 159-165 (Mar. 1, 2008).

Griffith, E., and Akella, S., "Coordinating Multiple Droplets in Planar Array Digital Microfluidics System," Algorithmic Foundations of Robotics, vol. 17, pp. 219-234 (Oct. 12, 2005).

Griffith, E.J. et al., "Performance Characterization of a Reconfigurable Planar-Array Digital Microfluidic System,"IEEE TCAD, vol. 25, Issue 2, pp. 340-352 (Feb. 2006).

Mitra, D., et al., "Accelerated Functional Testing of Digital Microfluidic Biochips," in Proceedings of the 17th Asian Test Symposium (ATS 2008), pp. 295-300 (Nov. 24-27, 2008).

Paik, P., et al., "Electrowetting-based Droplet Mixers for Microfluidic Systems," Lab-on-a-Chip, vol. 3, pp. 28-33 (Feb. 3, 2003).

Paik, P., et al., "Rapid Droplet Mixers for Digital Microfluidic Systems," Lab-on-a-Chip, vol. 3, pp. 253-259 (Sep. 12, 2003).

Ren, H. et al., "Design and Testing of an Interpolating Mixing Architecture for Electrowetting-Based Droplet-On-Chip Chemical Dilution," 12th International Conference on Transducers, Solid-State Sensors, Actuators and Microsystems, vol. 1, pp. 619-622 (Jun. 8-12, 2003).

Srinivasan, V., et al.,"An Integrated Digital Microfluidic Lab-on-a-Chip for Clinical Diagnostics on Human Physiological Fluids," Lab-on-a-Chip, vol. 4, No. 4, pp. 310-315, (2004).

Urbanski, J.P., et al., "Digital Microfluidics using Soft Lithography,"Lab Chip, vol. 6, No. 1, pp. 96-104 (2006).

Xu, T., and Chakrabarty, K., Functional Testing of Digital Microfluidic biochips, in Proceedings of the IEEE International Test Conference (ITC 2007), pp. 1-10 (Oct. 21-26, 2007).

\* cited by examiner

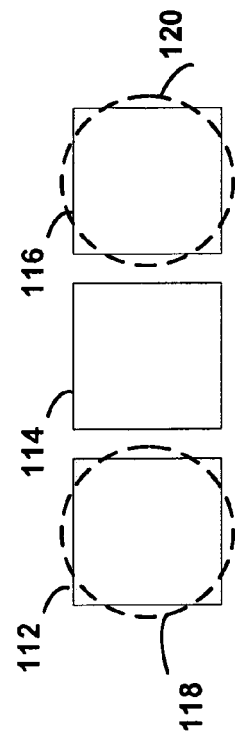
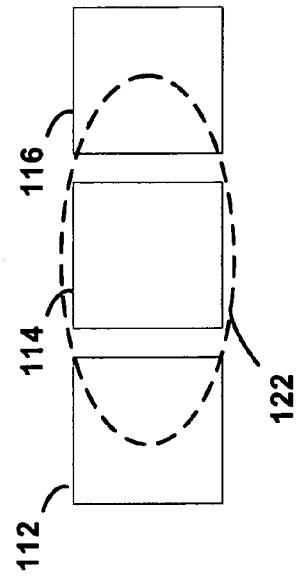
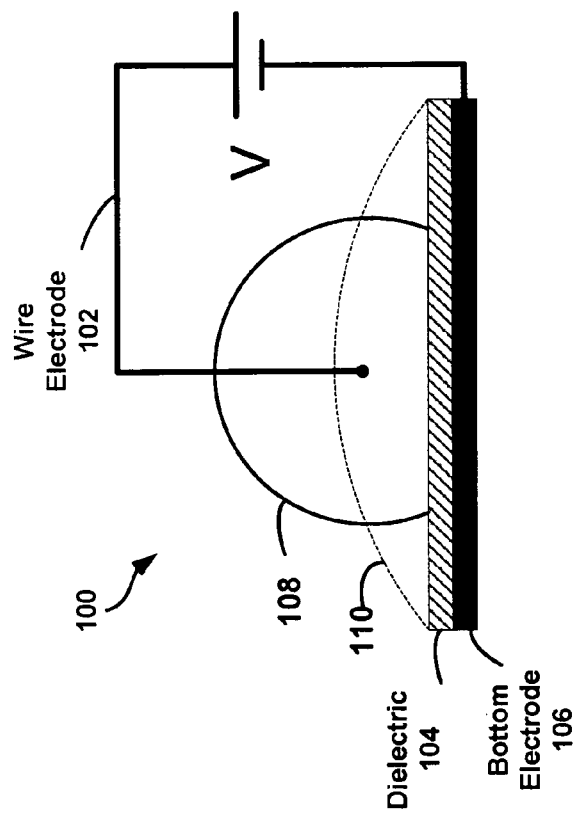
FIG. 1A
FIG. 1B
FIG. 1C

ARCHITECTURAL LAYOUT FOR DILUTION WITH REDUCED WASTAGE IN DIGITAL MICROFLUIDIC BASED LAB-ON-A-CHIP

CROSS-REFERENCE TO RELATED APPLICATION

This application is a U.S. Nationalization of PCT International Application No. PCT/IB2010/002899 filed Nov. 12, 2010, which claims priority under 35 U.S.C. §119(d) to a corresponding patent application filed in India and having application number 770/KOL/2010 filed on Jul. 15, 2010, the entire contents of each of the foregoing applications are herein incorporated by reference.

TECHNICAL FIELD

This application relates generally to the design of a digital microfluidic (DMF) based biochip.

BACKGROUND

To meet the challenge of rising costs of laboratory diagnostics associated with prevalent diseases, such as cardiovascular disease, cancer, diabetes, HIV, etc., a new technology is emerging called "Lab-on-a-Chip (LOC)." LOC implements one or more biochemical laboratory protocols or assays on a small chip (e.g., one of a few square centimeters in area). Compared with traditional bench-top procedures, these biochips offer many advantages, namely low sample and reagent consumption, small likelihood of error due to minimal human intervention, and high throughput and high sensitivity.

One specific biochip, called a "digital microfluidic (DMF) biochip," is designed to integrate assay operations such as detection, as well as sample pre-treatment and sample preparation on one chip. Front-end diagnostic functions, such as dilution of a sample, can be carried out on-chip or by pre-processing during sample preparation outside the chip. Off-chip sample processing and sample preparation may pose a significant hindrance to the overall biochemical assay time, due to long lead times that may be required for laboratory processes. Therefore, it may be desired that for fast and high throughput applications, sample pre-processing steps, such as sample dilution, be automated on-chip, i.e., integrated and self-contained on the biochip itself.

One challenge associated with using digital microfluidic biochips for diluting samples/reagents is to use dilution algorithms that both minimize waste and require a relatively small number of dilution steps to achieve the desired target concentration.

SUMMARY

In accordance with one embodiment, an arrangement of DMF-based electrode platforms is provided and includes a mixing module, two or more sample reservoirs, one or more waste reservoirs, and a plurality of storage platforms. The arrangement also includes pathways that extend between the mixing module and the reservoirs, as well as a pathway leading away from the mixing module.

In another embodiment, a method for diluting a sample/reagent fluid on a digital microfluidic (DMF) biochip is provided. The method comprises transporting one or more fluid droplets from each of the two sample reservoirs to one of two mixing modules and mixing the one or more droplets together in the one of the two mixing modules. The method further comprises, one or more subsequent mixing steps, wherein each mixing step comprises transporting one or more droplets from either (i) one of the two sample reservoirs, or (ii) one or more storage platforms included on the DMF-based biochip to the one of the two mixing modules. Each given mixing step further comprises mixing together the at least one or more transported droplets with at least one droplet of a resultant mixture produced in a preceding mix step.

In a further embodiment, software instructions are provided that determine a sequence of mix steps that produce a target CF mixture from two input CF fluids. The software instructions further determine appropriate actuation sequences for enabling an arrangement of DMF-based electrode platforms to carry out the sequence of determined mix steps.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1A is an example of a DMF-based electrode platform.
FIG. 1B is an example 1×3 array of DMF-based electrode platforms with 2 separate droplets.
FIG. 1C is an example 1×3 array of DMF-based electrode platforms with 2 droplets mixed into one large droplet.

DETAILED DESCRIPTION

Figure 2:
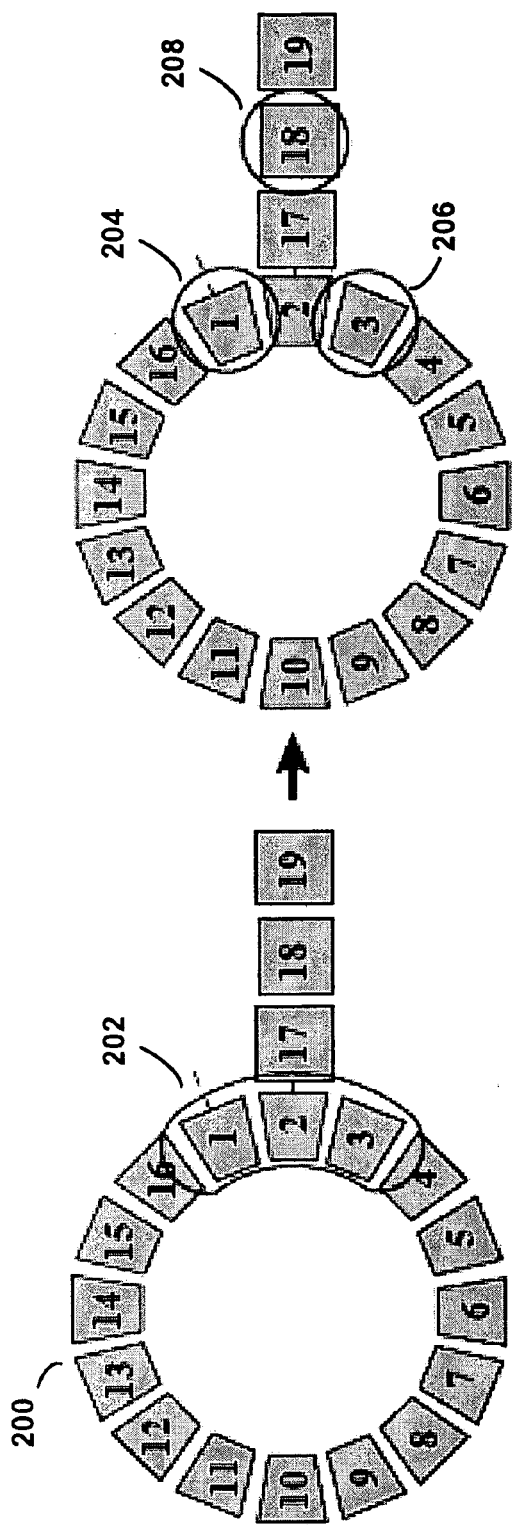
FIG. 2 is an illustration of an example 16-platform DMF rotary mixer splitting a 3 unit-volume droplet into 3 separate unit-volume droplets.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Digital microfluidic (DMF) biochips designed to perform dilution steps may utilize electrowetting-on-dielectric (EWOD) technology. EWOD technology revolves around changing the wettability of liquids on a dielectric surface by varying the electric potential through the liquid. By way of example, FIG. 1 illustrates a droplet resting on an example EWOD electrode 100 (referred to herein as a "platform"). A relatively low electric potential applied via a wire electrode 102 and a bottom electrode 106 may cause the droplet to form a rounded shape illustrated by the solid curve 108. A relatively high electric potential applied via the wire electrode 102 and the bottom electrode 106 may cause the droplet to flatten out in the manner illustrated by the dashed curve 110. DMF-based electrode platforms, such as the one illustrated in FIG. 1, may be adjacently positioned, such that the application and de-application of electric potential to the platforms may cause a droplet to move from platform to platform. Further, the platforms may be positioned on the chip in such a way that the mixing of two or more droplets is carried out by causing the droplets to combine across one or more platforms. In addition to EWOD technology, other methods for carrying out mixing and splitting steps on a droplet-based microfluidic biochip may exist as well, such as utilizing surface acoustic waves, or optoelectrowetting.

In an example of a DMF-based biochip, dielectric 104 and bottom electrode 106 may be encapsulated in a boro-aluminosilicate glass substrate (not shown). A chromium layer (e.g., of 5 nm) and a gold layer (e.g., of 100 nm) may be deposited onto the glass substrate and patterned by standard photolithography and wet etching. The bottom electrode may be formed of indium-tin oxide. Dielectric layer 104 may be formed of Parylene C and patterned using photolithography. An additional layer (not shown) may be added to the dielectric 104 to make the surface hydrophobic (e.g., a 0.5% Teflon AF 1060 layer of 30 nm thickness). In some embodiments, the wire electrode 102 may take the form of plate electrode encapsulated in a glass substrate, similar to the bottom electrode 106.

Example droplet volumes that platforms might hold may be on the order of about 1-2 nL, though other volumes are possible as well, depending on the size of the platform. In some DMF biochips, it may not be possible to control the volume of fluid contained on a single platform. Therefore, the smallest volume of fluid that can be mixed in a mix step may be a droplet from one platform mixed with a droplet from an adjacent platform. A "unit-volume" may thus refer to the volume of a droplet able to be contained on one platform of a particular DMF biochip. Biochips may have different platform sizes depending on the overall size of the chip. Accordingly, different biochips may be associated with different unit-volumes, and may be chosen or designed as such depending on the application.

A particular digital microfluidic (DMF) biochip may include an array of platforms such as any of the example 1×3 array of platforms illustrated in FIG. 1B and FIG. 1C. FIG. 1B illustrates platforms 112, 114, and 116, with platforms 112 and 116 holding respective droplets 118 and 120. Note that a platform is considered to hold a droplet of unit-volume with some overlap with the adjacent platforms or any portion of the droplet can reside on the platform depending on its volume and the application, for example. An application of voltage to platform 114 and a de-application of voltage to platforms 112 and 116 may cause the droplets 118 and 120 to be attracted to platform 114. This combination of droplets 122 across platforms is illustrated in FIG. 1C. The combination or resultant droplet 122 then has a volume of about twice the volume of individual droplets 118 or 120. A re-application of voltage to platforms 112 and 116 and a de-application of voltage to platform 114 can split the combination droplet 122 and result in the configuration illustrated in FIG. 1B.

A sequence of voltages applied to an array of platforms that cause droplets to move about the array can be referred to as an actuation sequence. The actuation sequence may be expressed as a bit pattern, with a 1 representing an application of voltage, and a 0 representing a de-application of voltage. For example, an actuation sequence that results in the mixture of droplets 118 and 120 across platforms 112, 114, and 116 (shown in FIGS. 1B and 1C) is illustrated in Table 1.

TABLE 1

| Time Step | Platform 112 | Platform 114 | Platform 116 |
|---|---|---|---|
| 0 | 1 | 0 | 1 |
| 1 | 0 | 1 | 0 |
| 2 | 1 | 0 | 1 |

At time step 0, platforms 112 and 116 are driven high while 114 is driven low, thus confining droplets 118 and 120 to respective platforms 112 and 116. At time step 1, platforms 112 and 116 are driven low while platform 114 is driven high. Both droplets are thus attracted to platform 114 and consequently mix together. Finally, at time step 2, platforms 112 and 116 are again driven high while platform 114 is driven low. This applies a splitting force to the resultant droplet 122, thus dividing the droplet into two substantially equal volume droplets and containing them on platforms 112 and 116 respectively.

FIG. 2 illustrates an example array of 19 platforms, 16 of which are arranged in a generally circular pattern to form a rotary mixer 200. Platforms 17-19 are arranged as a pathway leading away from the rotary mixer 200. Platforms 2 and 17 are adjacent. DMF rotary mixers, such as rotary mixer 200, may be used in DMF-based biochips since a rotary mixer can be used to mix multiple droplets together at the same time, as well as split one droplet from a combination of two or more droplets. Such functionality may be desirable in a biochip, depending on the application. Rotary mixer 200 illustrated in FIG. 2 has 16 platforms, though other rotary mixers may have different numbers of platforms.

FIG. 2 also illustrates a combination droplet 202, which has a combination of 3 unit-volumes of a fluid droplet, and spans platforms 1, 2, and 3 of rotary mixer 200. This combination droplet 202 can be split into three substantially equal droplets, of one unit-volume each, when the actuation sequence of Table 2 is carried out.

TABLE 2

| Time Step | Platform 1 | Platform 2 | Platform 3 | Platform 17 | Platform 18 | Platform 19 |
|---|---|---|---|---|---|---|
| 0 | 1 | 1 | 1 | 0 | 0 | 0 |
| 1 | 1 | 0 | 1 | 1 | 1 | 0 |
| 2 | 1 | 0 | 1 | 0 | 1 | 0 |

For example, at time step 0, platforms 1-3 are driven high, thus holding the combination droplet 202 across the three platforms. At time step 1, platform 2 is driven low while platforms 17 and 18 are driven high. This applies a splitting force in three ways as the combination droplet is pulled toward platforms 1, 3, and 17 simultaneously, or at about the same time. And at time step 2, platform 17 is driven low, thus resulting in one droplet 204 being held on platform 1, one droplet 206 being held on platform 206, and one droplet 208 being held on platform 18.

A digital microfluidic (DMF) biochip may be used to carry out the steps of an algorithm that solves a dilution problem. A dilution problem can be stated as: given a raw sample/reagent fluid (with 100% concentration) and a neutral buffer solution (with 0% concentration), determine a sequence of one-to-one (1:1) mixing and splitting steps for obtaining a desired concentration factor (CF) of the sample. CF is usually expressed as a percentage (e.g., 23%) or a fraction (e.g., 23/100) and can be thought of as a ratio of a volume of a raw sample to the final volume of the diluted sample after mixing with a buffer solution. An example reagent solution with CF of 100% could be a volume of saturated salt water solution, while an example buffer solution with CF of 0% could be a volume of distilled water.

In large-scale dilution applications, initial fluid samples (e.g., buffer solution and reagent fluid) may be in short supply. Therefore, when the dilution steps are designed to be carried out on a digital microfluidic (DMF) biochip, it may be desired that the steps use a relatively small amount of the initial fluid samples. Additionally, biochips may be on the order of a few square centimeters in size and so a sequence of mix and split steps that results in a relatively small amount of wastage may be desired as well.

Figure 3:
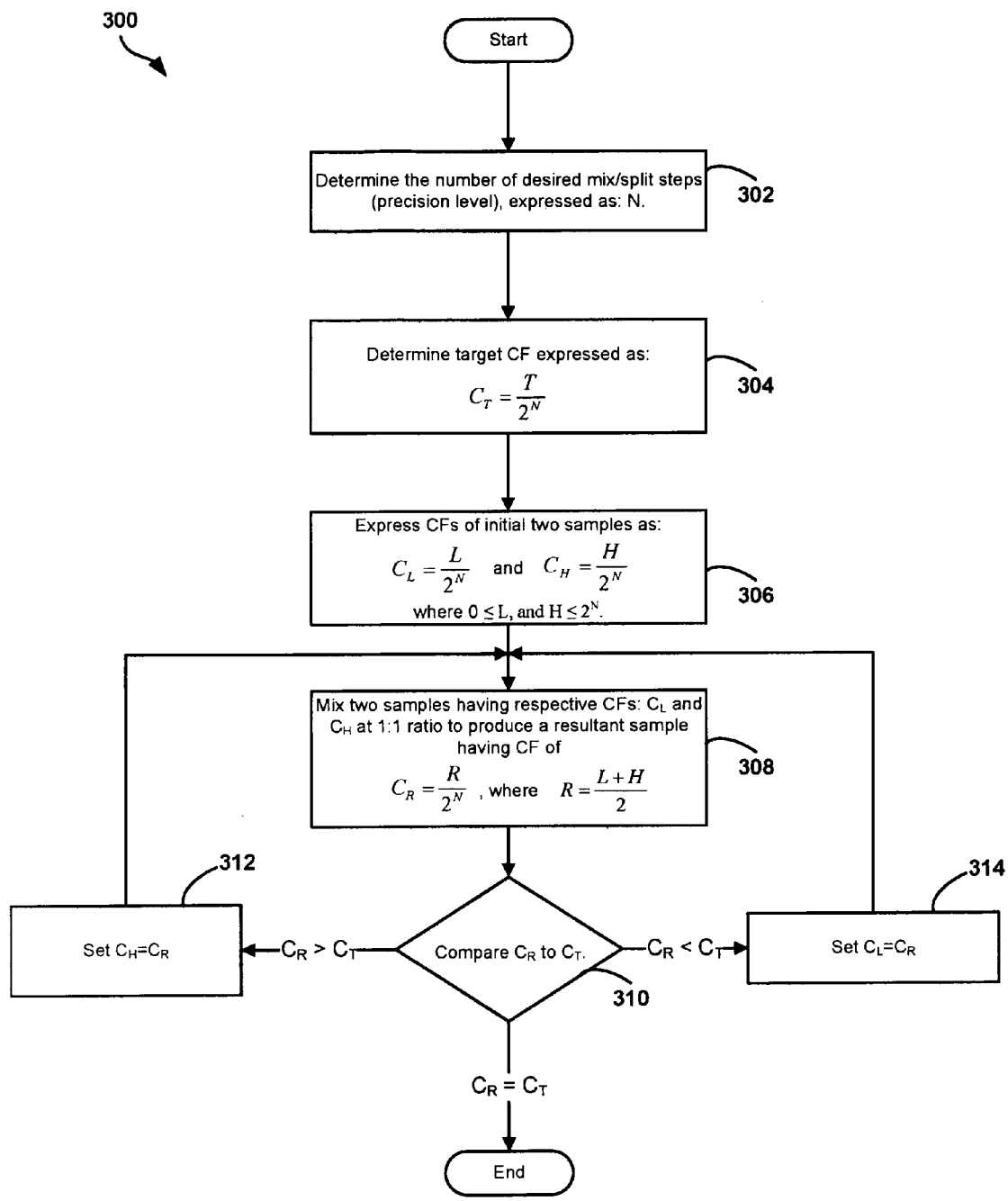
FIG. 3 is a flow chart illustrating an example algorithm for determining a sequence of mix steps used to produce a fluid with a target concentration factor.

One such example algorithm for determining and carrying out a sequence of mix/split steps that result in a relatively small amount of wastage, and use a relatively small amount of initial fluid samples, is illustrated in the flow chart 300 in FIG. 3. The illustrated algorithm is applicable to instances where a supplied reagent fluid (or raw sample) has a CF of 100% and a buffer solution has a CF of 0%, in addition to instances where the supplied reagent fluid has a CF of less than 100% and the buffer solution has a CF of greater than 0%. In all cases, the concentration factor of the initial reagent fluid can be expressed as $C_H$, the concentration factor of the buffer solution can be expressed as $C_L$, and the desired concentration factor (or target concentration factor) can be expressed as $C_T$, where $0\% \leq C_L < C_T < C_H \leq 100\%$.

The flow 300 begins at step 302 where the desired number of mix/split steps is chosen and expressed as an integer N. After N (or less) mix/split steps, a resultant solution is produced having the desired target concentration with an error limited to $\pm 1/2^N$. Therefore, N can also be thought of as a precision level, since the larger N is, the more precise the target concentration can be.

Continuing at step 304, a target CF is expressed as a rational number with a denominator of $2^N$. For example, in a case where N is chosen as 10, a desired target CF may be expressed as:

$$C_T = \frac{T}{1024}$$

The numerator, T, may be chosen as any number depending on the application. A T=313, for example, may equate to a target CF of:

$$C_T = \frac{313}{1024} \approx 30.6\%$$

At step 306, the CFs of the initial two samples (e.g., a reagent fluid and a buffer solution) are also expressed as rational numbers with denominators of $2^N$. The initial sample with the lower CF is labeled as $C_L$, and the initial sample with the higher CF is labeled as $C_H$. For example, in a case where N is chosen as 10, and the lower input sample has a CF of 0% and the higher input sample has a CF of 100%, $C_L$ may be expressed as:

$$C_L = \frac{0}{1024}$$

and $C_H$ may be expressed as:

$$C_H = \frac{1024}{1024}$$

At step 308, samples with concentration factors of $C_L$ and $C_H$ are mixed in a 1:1 volume ratio. It should be understood that a 1:1 ratio may be any ratio in which both reactants have about equal volumes. Thus, a 1:1 ratio encompasses a 2:2, 3:3, or k:k ratio (where k is a whole number). The resultant mixture of step 308 has a CF that is an average of the $C_L$ and $C_H$ values, and may be expressed as:

$$C_R = \frac{R}{2^N}$$

where:

$$R = \frac{L + H}{2}$$

For example, if a unit-volume of fluid with CF expressed as:

$$C_L = \frac{0}{1024}$$

were mixed with a unit-volume fluid with CF expressed as:

$$C_H = \frac{1024}{1024}$$

the resultant mixture would be 2 unit-volumes of fluid with a CF expressed as:

$$C_R = \frac{\frac{0 + 1024}{2}}{1024} = \frac{512}{1024}$$

After mixing in step 308, the flow continues at step 310 where the CF of the resultant mixture is compared with the target CF. Naturally, if the CF of the resultant mixture is equal to $C_T$ (or within an allowable error of about $\pm 1/2^N$ of the $C_T$), then the flow ends. If the resultant CF is greater than the target CF, then the resultant mixture is mixed with the lower of the two CFs used in the last mix step. This is illustrated in the flow by resetting the pointer $C_H$ to be equal to $C_R$ at step 312 and continuing the flow at mix step 308. If the resultant CF is less than the target CF, then the resultant mixture is mixed with the higher of the two CFs used in the last step. This is illustrated in the flow by resetting the pointer $C_L$ to be equal to $C_R$ at step 314 and continuing the flow at mix step 308. In this manner, the resultant mixture of each mix step approaches the target CF.

Figure 4:
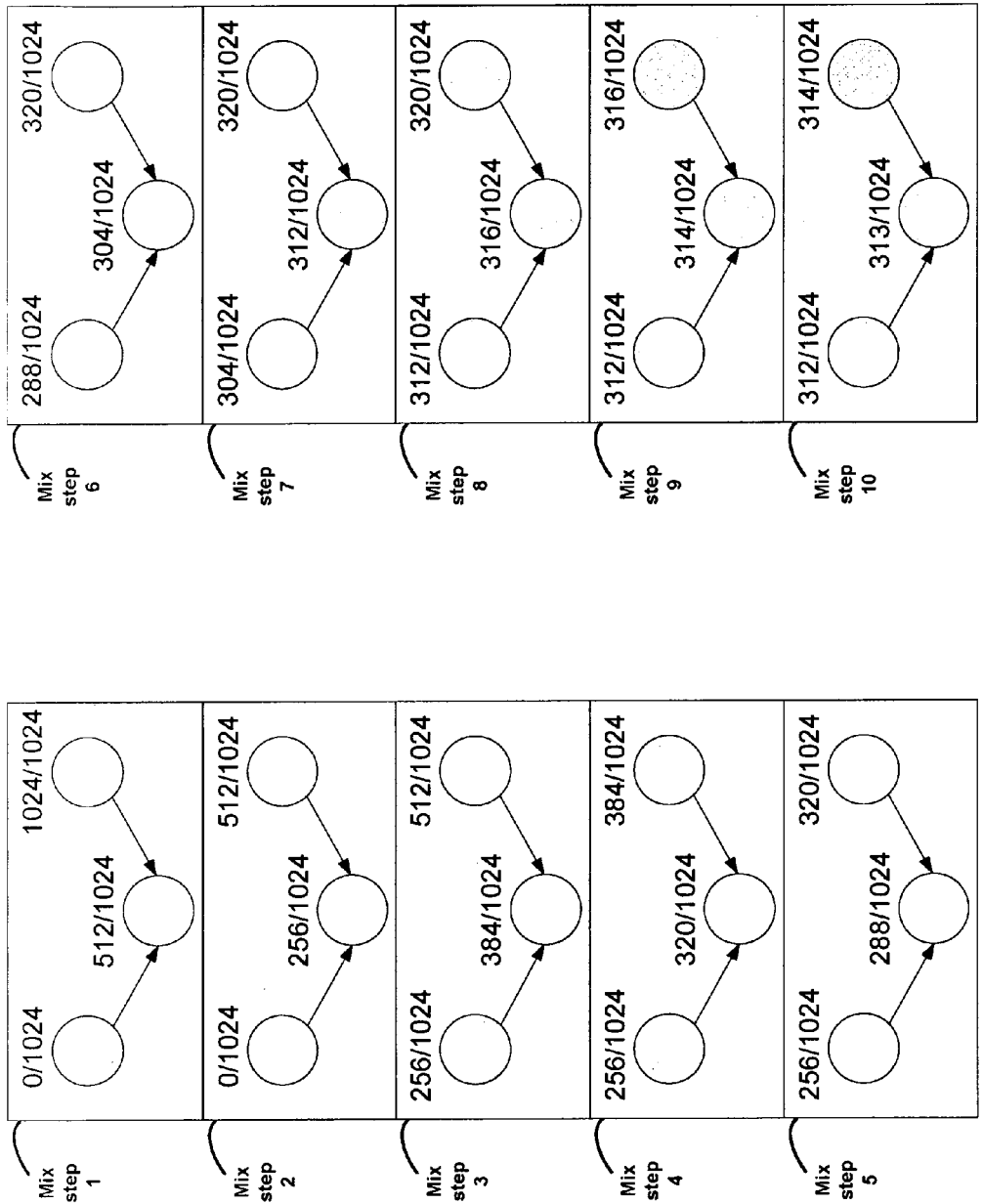
FIG. 4 is an example sequence of mix steps used to produce a fluid with a specific target concentration factor.

FIG. 4 illustrates an example sequence of mix steps according to the algorithm described in flow chart 300. In this example, 10 is chosen as the precision level, and therefore all the CFs are expressed with denominators of $2^{10}=1024$. The initial samples have CFs 0/1024 and 1024/1024, and a target CF is 313/1024 for this example. Thus, for mix step 1, $C_L=0/1024$, $C_H=1024/1024$, and $C_R=512/1024$. Since for each mix step the $C_L$ and $C_H$ are mixed at a 1:1 ratio, the numerator of the $C_R$ can be calculated by taking the average of the numerators of the $C_L$ and $C_H$. In mix step 1, for example, the $C_R$ numerator, 512, is the average of the $C_L$ numerator, 0, and the $C_H$ numerator, 1024.

The resultant mixture of mix step 1 is larger than the target CF of 313/1024, therefore in the next mix step, the resultant of mix step 1 should be mixed with the smaller of the $C_L$ and $C_H$ used in mix step 1. This can be seen in mix step 2 as the 512/1024 mixture is mixed with the 0/1024 sample to produce a 256/1024 resultant. This 256/1024 resultant, having a smaller CF than the target 313/1024, is mixed with 512/1024 (the greater of the $C_L$ and $C_H$ used in mix step 2) in mix step 3. Mix step 3 thus produces a resultant having a CF of 384/1024.

The mix steps in FIG. 4 proceed in this manner, producing resultants having CFs of 320/1024 in mix step 4, 288/1024 in mix step 5, 304/1024 in mix step 6, 312/1024 in mix step 7, 316/1024 in mix step 8, 314/1024 in mix step 9, and finally the target CF, 313/1024 in mix step 10.

Figure 5:
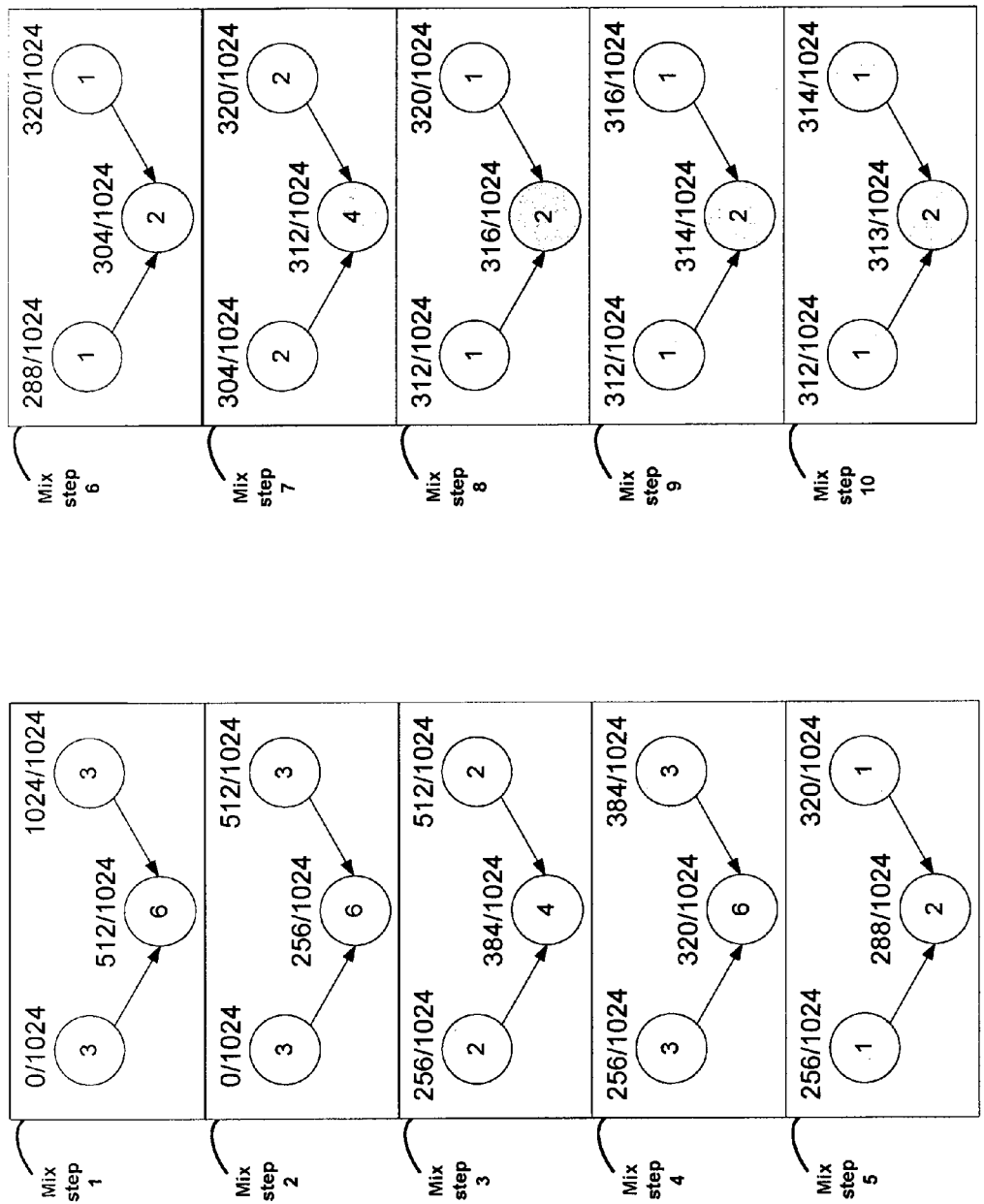
FIG. 5 is the example sequence of mix steps of FIG. 4 with numerals (inside the circles) indicating the number of unit-volumes to be utilized.

One way to reduce an amount of wastage that results from a sequence of mix steps is, in each step, to mix together only the amount of solution (or about the amount of solution) that is needed in subsequent steps to produce the target CF. By way of example, FIG. 5 illustrates the sequence of mix and split steps of FIG. 4 with numerals (inside the circles) indicating the number of unit-volumes of each intermediate mixture used for producing 2 unit-volumes of the target CF in mix step 10. Depending on the application, other number of unit-volumes of the target CF may be desired as well (e.g., 4, 6, 8, etc.). Since each mix step in FIG. 5 is substantially a 1:1 mix step, the solutions being mixed together are shown as having equal volumes, and therefore, resultant mixture unit-volumes are multiples of 2.

A method may be used to determine the number of unit volumes of mixtures required in each mix step of a sequence of mix/split steps. In the example of FIG. 5, it has been determined that in mix step 10, 2 unit volumes of target CF 313/1024 are desired. This therefore requires 1 unit volume of 312/1024 to be mixed with 1 unit volume of 314/1024. In mix step 9, 314/1024 is the resultant CF. To determine how many unit volumes of 314/1024 are required to be produced in this step (with 2 unit volumes being the minimum), it is determined how many unit volumes of 314/1024 are needed in subsequent mixing steps. In this case, only 1 unit volume of 314/1024 is needed in any subsequent mixing step (mix step 10, in this example), and so the minimum 2 unit volumes of 314/1024 are to be produced in mix step 9. This thus requires 1 unit volume of each of the reactants in mix step 9 (312/1024 and 316/1024).

The method continues by determining how many unit volumes of 316/1024 are needed in mix step 8. Since only 1 unit volume of 316/1024 is needed any in any subsequent mix step (mix step 9, in this example), the minimum 2 unit volumes of 316/1024 are to be produced in mix step 8. This thus requires 1 unit volume of each of the reactants in mix step 8 (312/1024 and 320/1024).

In mix step 7 of the example, it is determined that 4 unit volumes of 312/1024 should be produced since 3 unit volumes of 312/1024 are needed in subsequent mix steps (1 unit volume in each of mix steps 8, 9, and 10). This thus requires 2 unit volumes of each of the reactants in mix step 7 (304/1024 and 320/1024).

The method continues for each given mix step, thus determining the unit volumes of the resultant solutions for given each mix step by determining the unit volumes of the resultant solution used in subsequent mix steps. The unit volumes for the reactants in each given mix step are determined by halving the number of unit volumes of the resultant solution (and rounding up). Carrying out the method for the remainder of mix steps in FIG. 5 has determined that 3 unit volumes of initial CF 1024/1024 are used in mix step 1, 3 unit volumes of initial CF 0/1024 are used in mix step 1, and 3 unit volumes of initial CF 0/1024 are used in mix step 2. Thus, in this example, 9 unit volumes of initial reactants are required. After the sequence of mix steps is carried out, 2 unit volumes of target CF are produced. Thus, the example sequence of mix steps produces 9−2=7 unit volumes of waste.

Figure 6:
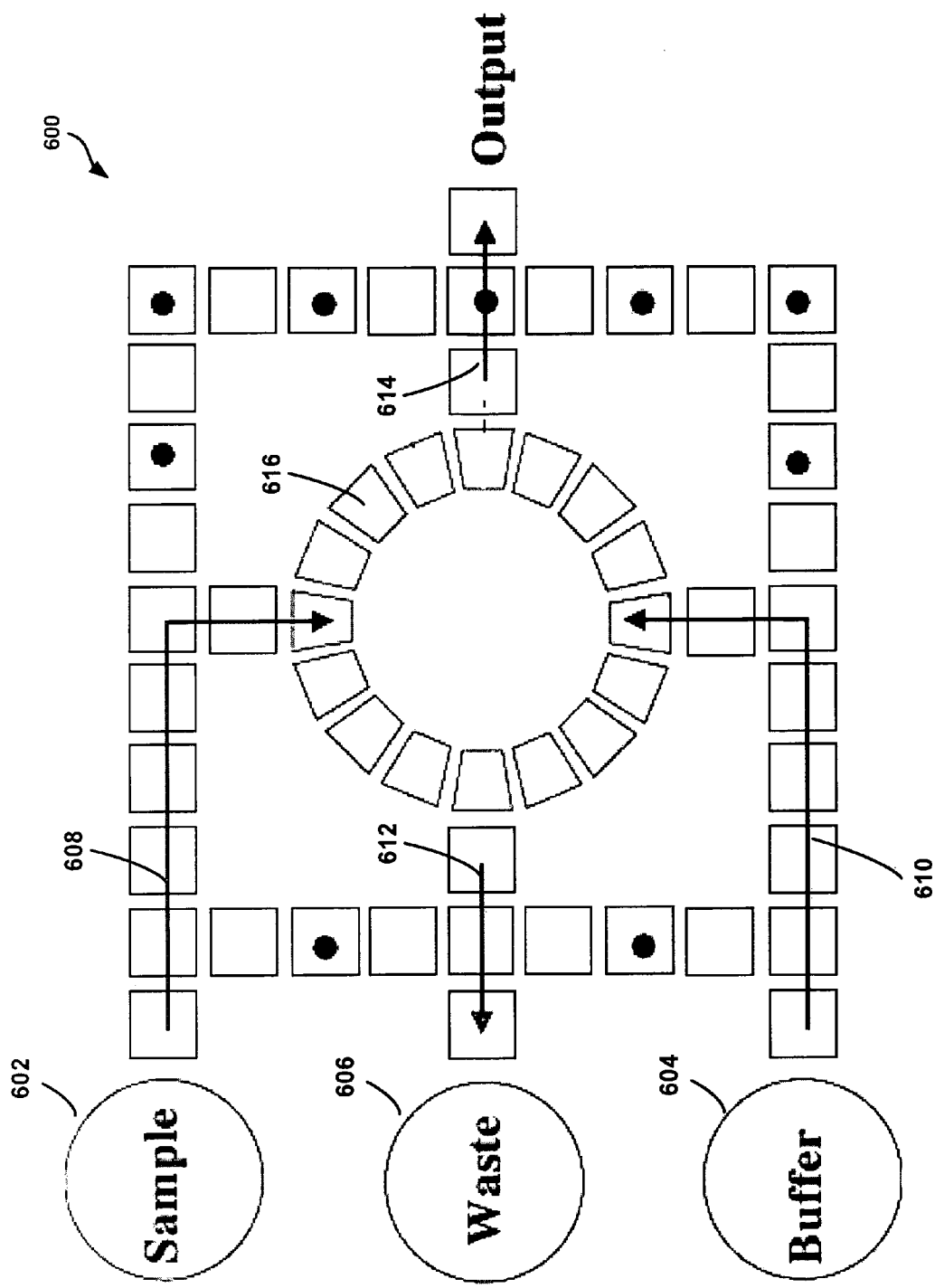
FIG. 6 is an example arrangement of DMF-based electrode platforms for carrying out a sequence of mix steps.

FIG. 6 illustrates an example arrangement 600 of EWOD platforms that may comprise a digital microfluidic biochip able to carry out the sequence of mix steps described by algorithm 300. The arrangement includes a sample reservoir 602, a buffer reservoir 604 (or second sample reservoir), and a waste reservoir 606. The arrangement also includes a mixing module to carry out mixing and splitting steps. The mixing module is illustrated as DMF rotary mixer 616 in the arrangement 600, but other mixing modules could be used as well, such as a matrix of platforms.

The arrangement 600 also includes a plurality of platforms that surround the DMF rotary mixer 616 and form pathways for droplets to travel to and from the reservoirs. For example, a plurality of platforms form sample pathway 608 and are able to transport droplets between the sample reservoir 602 and the rotary mixer 616. A plurality of platforms forming sample pathway 610 is able to transport droplets between sample reservoir 604 and rotary mixer 616. A plurality of platforms forming waste pathway 612 is able to transport droplets between the rotary mixer 616 and the waste reservoir 606. And a plurality of platforms forming output pathway 614 is able to transport droplets from the rotary mixer 616 to an output, such as outside the biochip.

Certain platforms in the arrangement 600 may be designated as storage platforms. The storage platforms can hold resultant droplets that are produced in intermediate mixing steps and are needed again in a subsequent mixing step. The possible locations of the storage platforms in arrangement 600 are identified with black dots. To satisfy fluidic constraints, and so that unintentional mixing does not take place, their positions are located with at least one electrode gap between two, diagonally or horizontally or vertically adjacent storage platforms. The positions of the storage platforms may be in locations such that the fluidic constraints are satisfied and no unintended mixing can occur.

The example mix steps illustrated in FIG. 5 may be carried out in the arrangement 600. Sample reservoir 602 may contain the 1024/1024 CF, while the sample reservoir 604 may contain the 0/1024 CF. Mix step 1 calls for 3 droplets of 0/1024 to be mixed with 3 droplets of 1024/1024 CF. Therefore, as a first step, the platforms comprising pathway 608 may be actuated in an appropriate sequence so as to cause 3 droplets of 1024/1024 CF to be transported from reservoir 602 to the rotary mixer 616. Simultaneously, the platforms comprising pathway 610 may be actuated in an appropriate sequence so as to cause 3 droplets of 0/1024 CF to be transported from sample reservoir 604 to the mixing module 616. When all of the droplets required for the mix step are contained on the platforms of the mixing module 616, an appropriate actuation sequence may cause the droplets to mix together, and after a certain amount of time required for mixing, form a resultant mixture of 6 droplets having a CF of 512/1024.

The sequence of mix steps illustrated in FIG. 5 indicates that 5 droplets of 512/1024 are needed in subsequent mixing steps (3 droplets in mix step 2, and 2 droplets in mix step 3). Therefore, 1 droplet of the 6 droplet mixture can be discarded. An appropriate platform actuation sequence may cause the rotary mixer to split 1 droplet from the 6 droplet mixture, and discard it via pathway 612. 3 droplets are needed for the next mix step (mix step 2), therefore those 3 droplets can remain in the mixing module while 2 droplets are transported to two of the storage platforms. An appropriate actuation sequence may split 2 droplets from the remaining 5 droplet mixture and transport each of the droplets to a different storage platform via one of the pathways.

Mix step 2 may be carried out by transporting 3 droplets of 0/1024 CF from sample reservoir 604 and mixing them with the three droplets of 512/1024 that remained in the rotary mixer 616 after the previous mix step. The resultant of mix step 2 is 6 droplets of 256/1024. 2 of these droplets are needed in the next mixing step, and 4 droplets are needed in subsequent mixing steps (3 droplets in mix step 4, and 1 droplet in mix step 5) Therefore, an appropriate actuation sequence may cause 4 droplets to be split from the 6 droplet resultant mixture and be transported to 4 different storage platforms.

Mix step 3 calls for mixing 2 droplets of 256/1024 with 2 droplets of 512/1024. 2 droplets of 256/1024 have remained in the mixing module 616 after the previous mix step, and two droplets of 512/1024 have been stored on two different storage platforms. Therefore, after the application of an appropriate actuation sequence that may cause the two 512/1024 droplets to be transported from the storage platforms to the mixing module 616, mix step 3 can take place at mixing module 616.

The mix steps of FIG. 5 continue in this manner by actuating the platforms of arrangement 600 in appropriate sequences. When the final mix step takes place, the mixing module 616 may split the droplets and transport them via output path 614.

The number of storage platforms and the number of platforms forming the mixing module 616 in arrangement 600 may be determined based on the application. For example, using the algorithm 300, it can be calculated that for a 2 droplet target CF, the maximum storage demand is based on the desired precision of the algorithm, and expressed as:

(N−2).

This can be seen in an example where N is chosen as 10, the target CF is chosen as 2 droplets of CF 513/1024, and the initial CFs are 0/1024 and 1024/1024. Table 3 illustrates 10 such mix steps that produce a target CF of 513/1024. Each row of Table 3 shows the higher and lower CF used in that particular step, as well as the number of droplets of higher and lower CF used in that particular step.

TABLE 3

| Step | Lower CF | Number of droplets of lower CF used | Higher CF | Number of droplets of higher CF used | Resultant CF | Number of droplets produced |
|---|---|---|---|---|---|---|
| 1 | 0/1024 | 5 | 1024/1024 | 5 | 512/1024 | 10 |
| 2 | 512/1024 | 1 | 1024/1024 | 1 | 768/1024 | 2 |
| 3 | 512/1024 | 1 | 768/1024 | 1 | 640/1024 | 2 |
| 4 | 512/1024 | 1 | 640/1024 | 1 | 576/1024 | 2 |
| 5 | 512/1024 | 1 | 576/1024 | 1 | 544/1024 | 2 |
| 6 | 512/1024 | 1 | 544/1024 | 1 | 528/1024 | 2 |
| 7 | 512/1024 | 1 | 528/1024 | 1 | 520/1024 | 2 |
| 8 | 512/1024 | 1 | 520/1024 | 1 | 516/1024 | 2 |
| 9 | 512/1024 | 1 | 516/1024 | 1 | 514/1024 | 2 |
| 10 | 512/1024 | 1 | 514/1024 | 1 | 513/1024 | 2 |

After the first mix step in Table 3 which produces 10 droplets of resultant CF 512/1024, 1 droplet of CF 512/1024 remains in the mixing module to be mixed in mix step 2. Since 8 droplets of CF 512/1024 are used in the subsequent mixing steps (1 droplet of CF 512/1024 is used in each of mix steps 3-10), those 8 droplets of CF 512/1024 will be stored on respective storage platforms of a DMF biochip until needed. The remaining one droplet of CF 512/1024 is not needed and may be discarded. Thus, the maximum droplet demand of an intermediate CF in a sequence of mix steps that produce 2 droplets of the target CF according to algorithm 300 is N−1 (which in the example illustrated in Table 3 is 9 droplets of CF 512/1024). And the maximum amount of storage platforms on a DMF biochip designed to produce 2 droplets of the target CF after N mix/split steps according to algorithm 300 is N−2.

Similarly, the number of platforms required for a DMF rotary mixer depends on the application as well. Using the example above, if the maximum demand for an intermediate CF droplet is (N−1), then to produce these (N−1) droplets, $$\left\lceil \frac{N-1}{2} \right\rceil$$

droplets are needed from each of the constituents. As an example, if N is chosen as 10, then the maximum demand for a particular CF is 10−1=9 droplets. To produce 9 droplets, 5 droplets of each of the constituents are needed. This is expressed by the expression:

$$\left\lceil \frac{N-1}{2} \right\rceil = \left\lceil \frac{9}{2} \right\rceil = \lceil 4.5 \rceil = 5.$$

So, the total number of droplets of the two constituents to be mixed is expressed by the expression:

$$2\left\lceil \frac{N-1}{2} \right\rceil = 2\left\lceil \frac{9}{2} \right\rceil = 2\lceil 4.5 \rceil = 2*5 = 10.$$

Since $$2\left\lceil \frac{N-1}{2} \right\rceil$$

droplets may need to be mixed together in one step, the rotary mixer should have at least that many platforms, and should include some additional platforms (e.g., 6 additional platforms) so that a mixture of $$2\left\lceil\frac{N-1}{2}\right\rceil$$

droplets can be rotated/stirred and effectively mixed. Therefore, the number of platforms that comprise the rotary mixer can be expressed as:

$$2\left\lceil\frac{N-1}{2}\right\rceil+6.$$

Figure 7:
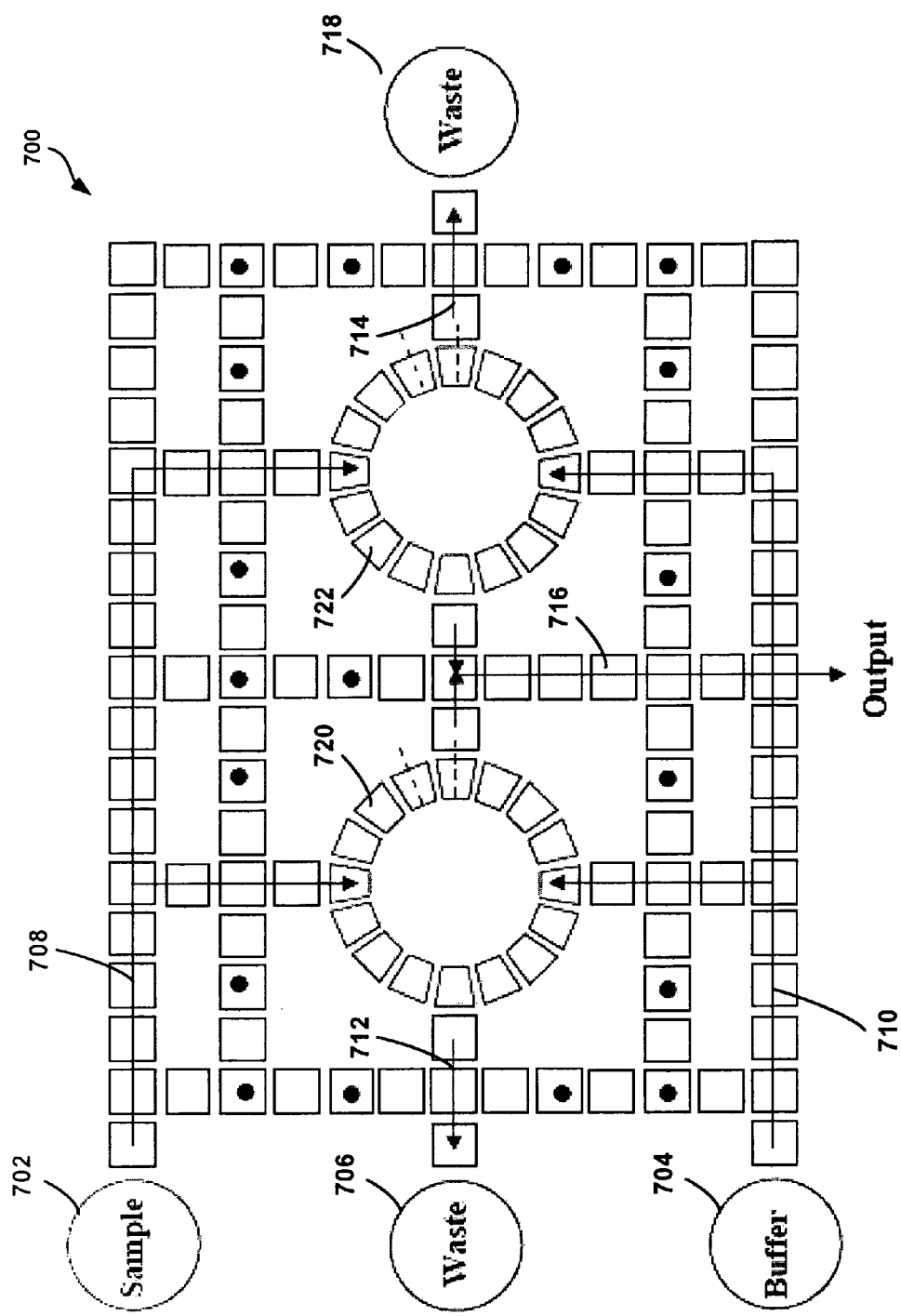
FIG. 7 is another example arrangement of DMF-based electrode platforms for carrying out a sequence of mix steps.

FIG. 7 illustrates another arrangement 700 of DMF-based electrode platforms designed to carry out a sequence of mix steps. The arrangement 700 is similar to the arrangement 600 in that the arrangement 700 includes sample reservoir 702, buffer reservoir (or second sample reservoir) 704, and waste reservoir 706. Rather than one rotary mixer, which is employed in the arrangement 600, the arrangement 700 employs two DMF rotary mixers 720 and 722 for parallel processing. The main objective of using two rotary mixers is to do parallel processing and reducing the inter-step droplet transportation time. While one rotary mixer, say 720, is carrying out the mix/split step 1 using CF 0/1024 and 1024/1024 producing the resultant CF 512/1024, other rotary mixer 722 can be loaded with the input sample droplet of CF 1024/1024 and as soon as resultant droplet of CF 512/1024 is produced in rotary mixer 720 it can be transported to the rotary mixer 722 very fast. This advantage is applicable to the subsequent mix/split steps also. Again, parallel processing, for example, may be used to carry out a first sequence of mix/split steps to produce a first target CF at one rotary mixer, while the other rotary mixer is used to simultaneously carry out a second sequence of mix/split steps to produce a second target CF.

Alternatively, the same sequence of mix/split steps can be carried out simultaneously on both rotary mixers to produce more than 2 droplets of the target CF (e.g., 4, 6, 8, etc.). Carrying out at one rotary mixer a sequence of mix/split steps designed to produce 2 droplets of a target CF, while simultaneously carrying out the same sequence of mix/split steps designed to produce 2 droplets of the target CF on another rotary mixer may produce the 4 target droplets faster than if the sequence was designed to produce 4 droplets of the target CF on a single rotary mixer. Additionally, more than two rotary mixers may be used for faster processing at the expense of chip area.

The arrangement 700 also includes a plurality of platforms forming sample pathway 708 which is able to transport droplets between sample reservoir 702 and the rotary mixers 720 and 722. Sample pathway 710 is included as well, which is able to transport droplets between the sample reservoir 704 and the rotary mixers 720 and 722. A plurality of platforms forming waste pathway 712 is able to transport droplets between rotary mixer 720 and waste reservoir 706, while a plurality of platforms forming waste pathway 714 is able to transport droplets between rotary mixer 722 and a second waste reservoir 718. Output pathway 716 is included as well and is able to transport droplets from rotary mixers 718 and 720 to an output, such as outside the biochip.

Potential locations of storage platforms in the arrangement 700 are illustrated with black dots. Since arrangement 700 is shown with two rotary mixers 720 and 722, a maximum of $$2(N-2)$$

storage locations may be needed.

Figure 8:
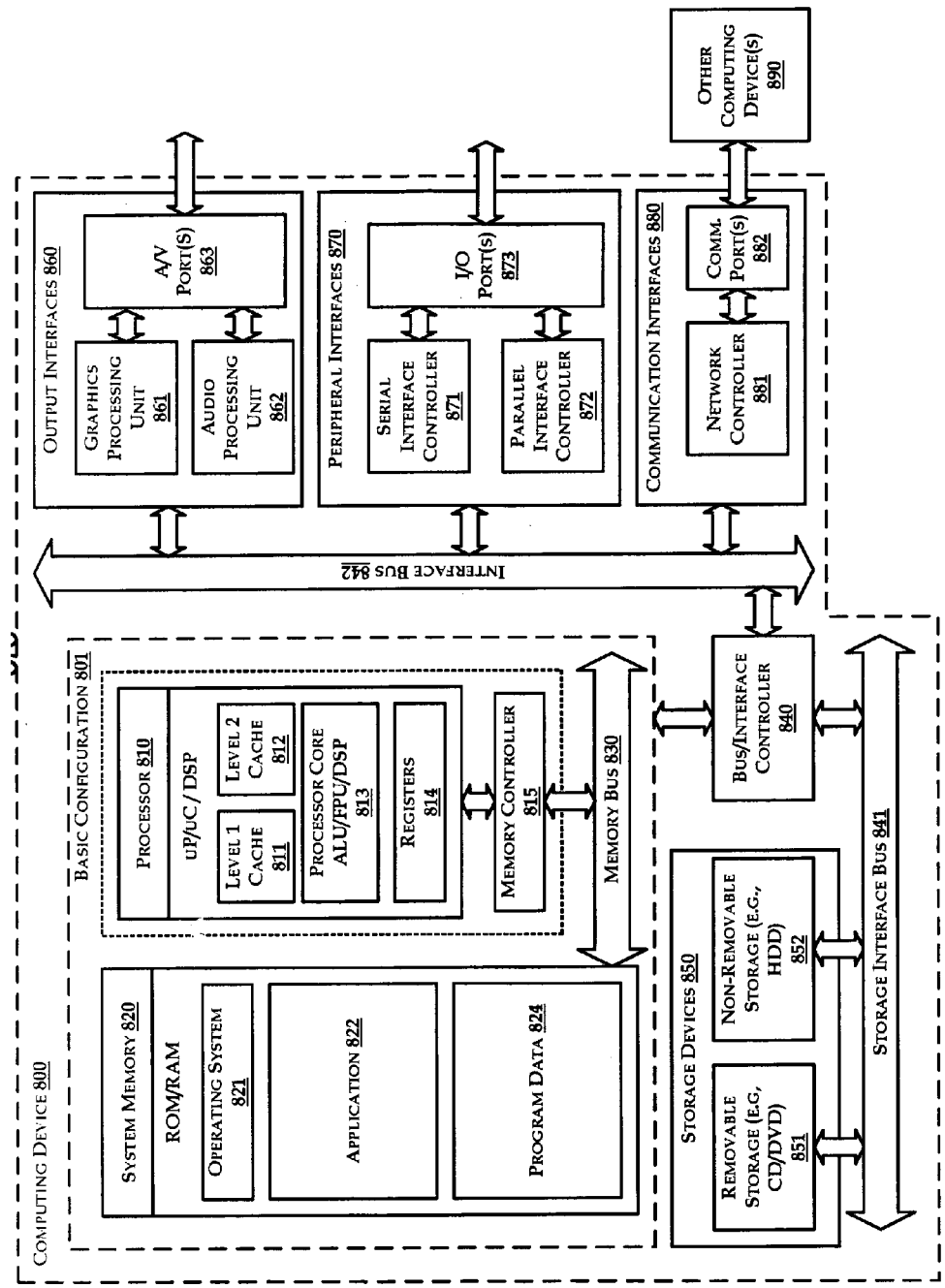
FIG. 8 is a block diagram illustrating an example computing device arranged for generating software instructions to carry out one or more methods described herein.

FIG. 8 is a block diagram illustrating an example computing device 800 that may be associated with a biochip. All or part of computing device 800 may be embedded within a biochip, or a biochip may be designed to couple with all or part of computing device 800 outside of the biochip (e.g., to receive instructions).

In a very basic configuration 801, computing device 800 typically includes one or more processors 810 and system memory 820. A memory bus 830 can be used for communicating between the processor 810 and the system memory 820.

Depending on the desired configuration, processor 810 can be of any type including but not limited to a microprocessor (µP), a microcontroller (µC), a digital signal processor (DSP), or any combination thereof. Processor 810 can include one more levels of caching, such as a level one cache 811 and a level two cache 812, a processor core 813, and registers 814. The processor core 813 can include an arithmetic logic unit (ALU), a floating point unit (FPU), a digital signal processing core (DSP Core), or any combination thereof. A memory controller 815 can also be used with the processor 810, or in some implementations the memory controller 815 can be an internal part of the processor 810.

Depending on the desired configuration, the system memory 820 can be of any type including but not limited to volatile memory (such as RAM), non-volatile memory (such as ROM, flash memory, etc.) or any combination thereof. System memory 820 typically includes an operating system 821, one or more applications 822, and program data 824.

Application 822 may include all or part of the disclosed algorithms. For example, application 822 may receive as an input the desired target concentration factor, the desired unit volume of the target concentration factor, the concentration factors of the initial reagent and buffer solutions, and the precision level i.e., the value of N. The application 822 may responsively determine the appropriate mix/split steps to achieve the desired volume of the target concentration factor. Further, application 822 may determine instructions for carrying out the determined mix/split steps as well. For example, in an DMF device associated with computing device 800, these instructions may comprise appropriate actuation sequences for causing an array of DMF-based electrode platforms to carry out the determined mix/split steps. Such instructions may take the form of a bit pattern/bit stream, called the actuation sequence for the addressable array of DMF-based electrodes.

In order to cause the DMF-based electrode platforms to carry out the determined sequence of mix steps, the appropriate actuation sequences may be fed to one or more peripheral interfaces. The I/O ports 873 may be coupled to the platforms, and based on the received actuation sequences, apply voltages to the platforms such that the determined sequence of mix steps is carried out.

Computing device 800 can have additional features or functionality, and additional interfaces to facilitate communications between the basic configuration 801 and any required devices and interfaces. For example, a bus/interface controller 840 can be used to facilitate communications between the basic configuration 801 and one or more data storage devices 850 via a storage interface bus 841. The data storage devices 850 can be removable storage devices 851, non-removable storage devices 852, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 820, removable storage 851 and non-removable storage 852 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media can be part of device 800.

Computing device 800 can also include an interface bus 842 for facilitating communication from various interface devices (e.g., output interfaces, peripheral interfaces, and communication interfaces) to the basic configuration 801 via the bus/interface controller 840. Example output interfaces 860 include a graphics processing unit 861 and an audio processing unit 862, which can be configured to communicate to various external devices such as a display or speakers via one or more A/V ports 863. Example peripheral interfaces 860 include a serial interface controller 871 or a parallel interface controller 872, which can be configured to communicate with external devices such as input devices (e.g., keyboard, mouse, pen, voice input device, touch input device, etc.) or other peripheral devices (e.g., printer, scanner, etc.) via one or more I/O ports 873. An example communication interface 880 includes a network controller 881, which can be arranged to facilitate communications with one or more other computing devices 890 over a network communication via one or more communication ports 882. The Communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media (or medium) as used herein can include both storage media and communication media.

Computing device 800 can be implemented as a portion of a digital microfluidic biochip. Computing device 800 can also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or materials, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A digital microfluidic (DMF) device including one or more electrode platforms, each electrode platform being configured to hold a fluid droplet and to transport the fluid droplet to an adjacent electrode platform, the device comprising:
   a plurality of electrode platforms forming a circular rotary mixing module, wherein the circular rotary mixing module is configured to move fluid droplets in a circular pattern while mixing the fluid droplets;
   two or more sample reservoirs for supplying fluid droplets;
   one or more waste reservoirs for collecting waste droplets;
   a first sample pathway of electrode platforms extending between one of the two sample reservoirs and one of the plurality of electrode platforms forming the circular rotary mixing module for transporting fluid droplets from the one of the two sample reservoirs to the circular rotary mixing module;
   a second sample pathway of electrode platforms extending between the other of the two sample reservoirs and one of the plurality of electrode platforms forming the circular rotary mixing module for transmitting fluid droplets from the other of the two sample reservoirs to the circular rotary mixing module;
   a waste pathway of electrode platforms extending between one of the plurality of electrode platforms forming the circular rotary mixing module and a waste reservoir for transporting waste droplets from the circular rotary mixing module to the waste reservoir;
   a plurality of storage electrode platforms positioned adjacent to, but not part of, the circular rotary mixing module, wherein each of the plurality of storage electrode platforms has access to one of the electrode platforms of one of the pathways such that fluid droplets can be transported between the plurality of storage electrode platforms and the circular rotary mixing module;
   a second plurality of electrode platforms arranged in a circular pattern forming a second circular rotary mixing module,
   wherein the first sample pathway also extends between one of the two sample reservoirs and one of the second plurality of electrode platforms forming the second circular rotary mixing module, and
   wherein the second sample pathway also extends between the other of the two sample reservoirs and one of the second plurality of electrode platforms forming the second circular rotary mixing module, and
   wherein the output pathway also extends from one of the second plurality of electrode platforms forming the second circular rotary mixing module;
   a second waste reservoir;
   a second waste pathway of electrode platforms extending between one of the second plurality of electrode platforms forming the second circular rotary mixing module and the second waste reservoir; and
   an output pathway of electrode platforms extending between the first plurality of electrode platforms forming the first circular rotary mixing module and the second plurality of electrode platforms forming the second circular rotary mixing module.

2. The device of claim 1, wherein the number of platforms in the plurality of platforms forming the circular rotary mixer is expressed by the expression:

$$2\left\lceil \frac{(N-1)}{2} \right\rceil + 6,$$

where N is the greater of (i) the number of the one or more subsequent mixing steps and (ii) 4.

3. The device of claim 1, wherein the number of platforms in the plurality of storage platforms is expressed by the expression:

(N−2).

4. The device of claim 1, wherein there is a greater number of storage platforms in the plurality of storage platforms than the plurality of platforms forming the circular rotary mixer, and
   wherein there is a greater number of storage platforms in the plurality of storage platforms than the second plurality of platforms forming the second circular rotary mixer.

5. The device of claim 1, wherein the number of platforms in the plurality of platforms forming the circular rotary mixer is equal to the number of platforms in the second plurality of platforms forming the second circular rotary mixer.

6. The device of claim 5, wherein the number of platforms in the plurality of platforms forming the circular rotary mixer is expressed by the expression:

$$2\left\lceil \frac{(N-1)}{2} \right\rceil + 6,$$

where N is the greater of (i) the number of the one or more subsequent mixing steps and (ii) 4.

7. The device of claim 1, wherein the number of platforms in the plurality of storage platforms is expressed by the expression:

2(N−2).

8. The device of claim 1, wherein the arrangement is contained in a single digital microfluidic biochip.

9. The device of claim 1, wherein when a droplet is stored on each storage platform of the plurality of storage platforms, each of the stored droplets can be transported to one of the platforms of one of the pathways.

10. An arrangement of digital microfluidic (DMF) based electrode platforms, each electrode platform being configured to hold a fluid droplet and to transport the fluid droplet to an adjacent electrode platform, the arrangement comprising:
- a plurality of electrode platforms forming a circular rotary mixing module;
- two or more sample reservoirs for supplying fluid samples;
- one or more waste reservoirs for collecting waste droplets;
- a first sample pathway of electrode platforms extending between one of the two sample reservoirs and one of the plurality of electrode platforms forming the circular rotary mixing module;
- a second sample pathway of electrode platforms extending between the other of the two sample reservoirs and one of the plurality of electrode platforms forming the circular rotary mixing module;
- a waste pathway of electrode platforms extending between one of the plurality of electrode platforms forming the circular rotary mixing module and a waste reservoir;
- a plurality of storage electrode platforms, wherein each of the plurality of storage electrode platforms has access to one of the electrode platforms of one of the pathways;
- a second plurality of electrode platforms arranged in a generally circular pattern forming a second circular rotary mixing module,
- wherein the first sample pathway also extends between one of the two sample reservoirs and one of the second plurality of electrode platforms forming the second circular rotary mixing module, and
- wherein the second sample pathway also extends between the other of the two sample reservoirs and one of the second plurality of electrode platforms forming the second circular rotary mixing module, and
- wherein the output pathway also extends from one of the second plurality of electrode platforms forming the second circular rotary mixing module;
- a second waste reservoir;
- a second waste pathway of electrode platforms extending between one of the second plurality of electrode platforms forming the second rotary mixer and the second waste reservoir; and
- an output pathway of electrode platforms extending between the first plurality of electrode platforms forming the first rotary mixing module and the second plurality of electrode platforms forming the second mixing module.

* * * * *

UNITED STATES PATENT AND TRADEMARK OFFICE
CERTIFICATE OF CORRECTION

Page 1 of 2

PATENT NO. : 9,201,042 B2
APPLICATION NO. : 13/809494
DATED : December 1, 2015
INVENTOR(S) : Bhattacharya et al.

It is certified that error appears in the above-identified patent and that said Letters Patent is hereby corrected as shown below:

On the title page item (75), under "Inventors", in Column 1, Lines 1-2, delete "IN (US);" and insert -- (IN); --, therefor.

On the title page item (75), under "Inventors", in Column 1, Line 2, delete "IN (US);" and insert -- (IN); --, therefor.

In the Drawings,

In Fig. 3, Sheet 3 of 8, delete " ←—$C_R > C_T$— " and insert -- ←—$C_R > C_T$— --, therefor.

In Fig. 3, Sheet 3 of 8, delete " —$C_R < C_T$→ " and insert -- —$C_R < C_T$→ --, therefor.

In Fig. 8, Sheet 8 of 8, delete "uP/uC/DSP" and insert -- µP/µC/DSP --, therefor.

In the Specification,

In Column 1, Line 8, delete "Nationalization of" and insert -- Nationalization under 35 U.S.C. § 371 of --, therefor.

In Column 1, Line 10, delete "§119(d)" and insert -- § 119(d) --, therefor.

In Column 2, Line 37, delete "is the" and insert -- is an --, therefor.

In Column 5, Line 38, delete "flow 300" and insert -- flow chart 300 --, therefor.

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,201,042 B2

In Column 5, Line 60, delete " $C_T = \dfrac{313}{1024} \approx 30.6\%$ " and insert -- $C_T = \dfrac{313}{1024} \approx 30.6\%$ . --, therefor.

In Column 6, Line 14, delete " $C_H = \dfrac{1024}{1024}$ " and insert -- $C_H = \dfrac{1024}{1024}$ . --, therefor.

In Column 6, Line 55, delete " $C_E = \dfrac{\frac{0+1024}{2}}{1024} = \dfrac{512}{1024}$ " and insert -- $C_E = \dfrac{\frac{0+1024}{2}}{1024} = \dfrac{512}{1024}$ . --, therefor.

In Column 9, Line 51, delete "output path 614." and insert -- output pathway 614. --, therefor.

In Column 12, Line 46, delete "in an" and insert -- in a --, therefor.

In Column 13, Line 21, delete "device 800." and insert -- computing device 800. --, therefor.

In Column 13, Lines 30-31, delete "peripheral interfaces 860" and insert -- peripheral interfaces 870 --, therefor.